US012569345B2

(12) United States Patent
Vogt et al.

(10) Patent No.: US 12,569,345 B2
(45) Date of Patent: Mar. 10, 2026

(54) AUGMENTATION DEVICE

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 541 days.

(21) Appl. No.: 18/165,015

(22) Filed: Feb. 6, 2023

(65) Prior Publication Data

US 2023/0255777 A1    Aug. 17, 2023

(30) Foreign Application Priority Data

Feb. 11, 2022    (EP) ..................................... 22156256

(51) Int. Cl.
*A61F 2/30* (2006.01)

(52) U.S. Cl.
CPC ...... *A61F 2/30734* (2013.01); *A61F 2/30771* (2013.01); *A61F 2002/30205* (2013.01); *A61F 2002/30324* (2013.01); *A61F 2002/3069* (2013.01); *A61F 2002/30736* (2013.01); *A61F 2002/30807* (2013.01); *A61F 2002/3092* (2013.01)

(58) Field of Classification Search
CPC ........ A61F 2/30734; A61F 2002/30736; A61F 2/30767; A61F 2002/30205; A61F 2002/30209; A61F 2002/3021; A61F 2002/30217; A61F 2002/30334; A61F 2002/30738
See application file for complete search history.

(56) References Cited

U.S. PATENT DOCUMENTS

| | | | |
|---|---|---|---|
| 4,519,101 A | 5/1985 | Schreiber | |
| 10,932,913 B2 | 3/2021 | Vergari et al. | |
| 2003/0114476 A1 | 6/2003 | Plachetka et al. | |
| 2007/0118229 A1* | 5/2007 | Bergin | A61F 2/30771 623/23.46 |
| 2016/0287391 A1* | 10/2016 | Larsen | A61F 2/30907 |
| 2018/0200061 A1 | 7/2018 | Bauer et al. | |
| 2021/0228366 A1* | 7/2021 | Heggs | A61F 2/389 |
| 2023/0190475 A1* | 6/2023 | Gilson | A61F 2/38 623/20.16 |

FOREIGN PATENT DOCUMENTS

| | | |
|---|---|---|
| EP | 3319558 B1 | 10/2019 |
| EP | 3909549 A1 | 11/2021 |
| WO | 2022008441 A1 | 1/2022 |

* cited by examiner

*Primary Examiner* — Javier G Blanco
(74) *Attorney, Agent, or Firm* — Dicke, Billig & Czaja, PLLC

(57) ABSTRACT

The invention relates to an augmentation device comprising an annular cone surrounding a channel which extends axially along a longitudinal axis of the augmentation device from a proximal cone end to a distal cone end, wherein an outer diameter of the cone decreases from the proximal cone end in the direction of the distal cone end.

11 Claims, 8 Drawing Sheets

AUGMENTATION DEVICE

CROSS-REFERENCE TO RELATED APPLICATIONS

This application claims priority pursuant to 35 U.S.C. 119(a) to European Application No. 22156256.4, filed Feb. 11, 2022, which application is incorporated herein by reference in its entirety.

DESCRIPTION

The invention relates to an augmentation device comprising an annular cone surrounding a channel which extends axially along a longitudinal axis of the augmentation device from a proximal cone end to a distal cone end, wherein an outer diameter of the cone decreases from the proximal cone end in the direction of the distal cone end.

The subject matter of the invention is in particular an augmentation device for use in joint endoprostheses, in particular revision joint endoprostheses for knee or hip joints. The augmentation device according to the invention is suitable for strengthening or even partially replacing debrided bone tissue and thus allowing a joint endoprosthesis—in particular, a revision endoprosthesis—to be anchored securely and stably in a bone canal. In addition, the augmentation device according to the invention serves in particular to uniformly introduce force into the surrounding bone tissue during implantation of a joint endoprosthesis, in particular a revision joint endoprosthesis. In particular, the augmentation device can be explanted, while avoiding major losses of bone tissue.

BACKGROUND OF THE INVENTION

In orthopedic surgery, septic revisions of joint endoprostheses infected with microorganisms must unfortunately be carried out to a certain extent. In this case, the infected joint endoprostheses are explanted, and the infected or necrotic tissue is removed. This removal of infected/necrotic tissue is referred to as debridement. In this case, a substantial loss of bone tissue can occur in the region of the removed joint endoprosthesis—in particular in the case of previously damaged bone tissue substance, e.g., due to osteoporosis—which can lead to problems when anchoring a revision joint endoprosthesis. In order to strengthen or partially replace the remaining bone tissue and to ensure as uniform an introduction of force as possible into the remaining bone tissue during use of the revision joint endoprosthesis, one possible treatment option is the use of an augmentation device in the form of a metal cone. To this end, the infected bone tissue is removed, and the resulting cavity is filled by inserting the augmentation device. The conical design of the augmentation device serves to receive a stem of a prosthesis—in particular, a joint endoprosthesis or a revision joint endoprosthesis—in an axially extending channel of the augmentation device and to anchor it there, for example using bone cement. The augmentation device itself is designed such that it can be inserted into the cavity formed by debridement. In order to allow growth of newly forming bone tissue and thus firmly connect the augmentation device to the bone to be treated, the metal cones comprise a structured, e.g., roughened or spongiosa-like, surface structure on their lateral surface. Such an augmentation device is described, for example, in the patent specification U.S. Pat. No. 8,506,645 B2.

In order to meet the different anatomical conditions of patients, augmentation devices of different sizes—in particular, comprising different outer diameters—are available on the market.

In the case of septic revisions, despite careful debriding during the septic revision, the previously treated infection can flare up again, which makes it necessary to explant the augmentation device together with the revision joint endoprosthesis. Since the metal cones have grown together with the bone tissue due to their structured lateral surfaces, they can be explanted only with difficulty. The ingrown metal cones often have to be separated from the bone tissue with the aid of chisels and, due to the rigid structure of the cones, removed axially from the bone implant site. Both can lead to significant loss of bone tissue, which makes it even more difficult to implant a new prosthesis. In the case of massive bone tissue loss, the only remaining treatment option is the implantation of a tumor joint endoprosthesis, if the biomechanical function of the joint is to be largely preserved.

The patent specification EP 3 319 558 B1 describes an augmentation device whose outer diameter can be varied within certain limits. For this purpose, the augmentation device comprises an annular cone which comprises at least one axially extending flexural joint. The at least one joint allows the cone to be compressed by external pressure, which reduces the outer diameter of the augmentation device. By compressing the cone, an explantation of the augmentation device from the patient is facilitated.

A disadvantage when using joints—in particular, flexural joints—is that the augmentation device can be compressed only to a small extent, in order to reduce the outer diameter for facilitated explantation. Although the separation of cone and bone is simplified at the point of the joint, the part of the augmentation device that has been detached from the bone remains within the bone canal, which makes it more difficult to detach further parts of the augmentation device from the bone. In addition, bending of the joints leads to buckling of the metal cone—in particular, sharp-edged buckling—which increases the risk of injury to the surgeon and the patient. The buckled cone also makes handling within the bone canal more difficult for steric reasons.

An augmentation device is therefore desirable which, in the implanted state, allows growth, preferably ingrowth, of bone tissue on or at its surface and which can nevertheless be explanted easily, quickly, safely, and with only a minor loss of bone tissue.

OBJECTS

It is an object of the present invention to at least partially overcome one or more of the disadvantages resulting from the prior art.

In particular, an augmentation device is to be provided which allows growth, preferably ingrowth, of bone tissue on or at a surface of the augmentation device and which at the same time allows simple and safe explantation, with only minor losses of bone tissue. The augmentation device should be capable of being permanently or temporarily implanted in a patient.

PREFERRED EMBODIMENTS OF THE INVENTION

The features of the independent claims contribute to at least partially fulfilling at least one of the aforementioned objects. The dependent claims provide preferred embodiments which contribute to at least partially fulfilling at least one of the objects.

A first embodiment of the invention is an augmentation device comprising an annular cone surrounding a channel which extends axially along a longitudinal axis of the augmentation device from a proximal cone end to a distal cone end, wherein an outer diameter of the cone decreases—in particular, steadily decreases—from the proximal cone end in the direction of the distal cone end, wherein at least two metal plates—in particular, bent metal plates—following an outer contour of the cone are arranged on a lateral surface of the cone, wherein the cone is reversibly detachable from the metal plates by displacing the cone in the direction of the proximal cone end.

In one embodiment of the augmentation devices, the metal plates are spaced apart from one another by axially extending gaps between the metal plates. This embodiment is a second embodiment of the invention, which is preferably dependent upon the first embodiment of the invention.

In one embodiment of the augmentation devices, axially extending webs are formed on the metal surface of the cone, which webs engage in the gaps between the metal plates. This embodiment is a third embodiment of the invention, which is preferably dependent upon the second embodiment of the invention.

In one embodiment of the augmentation device, the webs comprise at least one web guide means which fluidically connects the proximal cone end to the distal cone end and/or the proximal cone end to a web outer surface, in particular a web outer surface facing the metal plates. This embodiment is a fourth embodiment of the invention, which is preferably dependent upon the third embodiment of the invention.

In one embodiment of the augmentation device, the cone comprises at least one cone guide means which fluidically connects the proximal cone end to the distal cone end. This embodiment is a fifth embodiment of the invention, which is preferably dependent upon one of the preceding embodiments of the invention.

In one embodiment of the augmentation device, the cone comprises a sliding element at the proximal cone end, which sliding element interacts with the metal plates at a proximal metal plate end facing the proximal cone end such that a force acting on the cone from the direction of the proximal cone end can be transmitted to the metal plates via the sliding element. This embodiment is a sixth embodiment of the invention, which is preferably dependent upon one of the preceding embodiments of the invention.

In one embodiment of the augmentation device, the metal plates are arranged on the lateral surface of the cone such that a reversible, form-fitting connection is formed between the metal plates and the lateral surface. This embodiment is a seventh embodiment of the invention, which is preferably dependent upon one of the preceding embodiments of the invention.

In one embodiment of the augmentation device, a cone wall thickness of the cone is greater than or equal to a metal plate wall thickness of the metal plates. This embodiment is an eighth embodiment of the invention, which is preferably dependent upon one of the preceding embodiments of the invention.

In one embodiment of the augmentation device, the metal plates cover at least 80% by area, preferably 85% by area, more preferably 90% by area, of the lateral surface of the cone. This embodiment is a ninth embodiment of the invention, which is preferably dependent upon one of the preceding embodiments of the invention.

In one embodiment of the augmentation device, the metal plate outer surface facing away from the lateral surface of the cone is roughened, porous, and/or comprises blind holes. This embodiment is a tenth embodiment of the invention, which is preferably dependent upon one of the preceding embodiments of the invention.

In one embodiment of the augmentation device, the blind holes comprise a diameter of less than 3 mm, preferably of less than 2 mm, and more preferably of less than 1 mm, wherein the diameter is preferably not smaller than 0.5 mm. This embodiment is an eleventh embodiment of the invention, which is preferably dependent upon the tenth embodiment of the invention.

In one embodiment of the augmentation device, the cone comprises feedthroughs which fluidically connect the channel to an intermediate space between the cone and the metal plates. This embodiment is a twelfth embodiment of the invention, which is preferably dependent upon one of the preceding embodiments of the invention.

In one embodiment of the augmentation device, a scraper element is arranged at a distal channel end facing the distal cone end. This embodiment is a thirteenth embodiment of the invention, which is preferably dependent upon one of the preceding embodiments of the invention.

In one embodiment of the augmentation devices, the metal plates comprise a biocompatible metal; in particular, the metal plates are made of a biocompatible metal. This embodiment is a fourteenth embodiment of the invention, which is preferably dependent upon one of the preceding embodiments of the invention.

In one embodiment of the augmentation device, the cone comprises a biocompatible polymer; in particular, the cone consists of a biocompatible polymer. This embodiment is a fifteenth embodiment of the invention, which is preferably dependent upon one of the preceding embodiments of the invention.

GENERAL

In the present description, range specifications also include the values specified as limits. An indication of the type "in the range of X to Y" with respect to a variable A consequently means that A can assume the values X, Y and values between X and Y. Ranges delimited on one side of the type "up to Y" for a variable A accordingly mean, as a value, Y and less than Y.

Some of the described features are linked to the term "substantially." The term "substantially" is to be understood as meaning that, under real conditions and manufacturing techniques, a mathematically exact interpretation of terms such as "superimposition," "perpendicular," "diameter," or "parallelism" can never be given exactly, but only within certain manufacturing-related error tolerances. For example, "substantially perpendicular axes" form an angle of 85 degrees to 95 degrees relative to one another, and "substantially equal volumes" comprise a deviation of up to 5% by volume. An "apparatus consisting substantially of plastic material" comprises, for example, a plastics content of $\geq 95$ to $\leq 100\%$ by weight. A "substantially complete filling of a volume B" comprises, for example, a filling of $\geq 95$ to $\leq 100\%$ by volume of the total volume of B.

The terms "proximal" and "distal" serve only to designate the spatially opposite ends of the augmentation device, the cone, or other structural units of the augmentation device and do not allow any conclusions to be drawn about the orientation of the augmentation device implanted in a human body. "Distally to . . . " and "proximally to . . . " or similar formulations correspondingly express only the spatial arrangement of two structural units of the augmentation device and the augmentation system in relation to one another.

DETAILED DESCRIPTION

A first subject matter of the invention relates to an augmentation device comprising an annular cone surrounding a channel which extends axially along a longitudinal axis of the augmentation device from a proximal cone end to a distal cone end, wherein an outer diameter of the cone decreases from the proximal cone end in the direction of the distal cone end, wherein at least two, in particular two, three, four, five or six metal plates, in particular bent metal plates, following an outer contour of the cone are arranged on a lateral surface of the cone, wherein the cone is reversibly detachable from the metal plates by displacing the cone in the direction of the proximal cone.

The augmentation device comprises an annular cone. A cone is a cone-shaped—in particular, truncated cone-shaped—component comprising a proximal cone end and a distal cone end axially opposite the proximal cone end, along the longitudinal axis of the augmentation device. The cone comprises an outer diameter which decreases from the proximal cone end in the direction of the distal cone end. The cone thus comprises the largest outer diameter at the proximal cone end and the smallest outer diameter at the distal cone end. Preferably, the outer diameter decreases steadily from the proximal cone end in the direction of the distal cone end.

The cone is annular, or, in other words, tubular. The annular cone thus encloses a channel which extends axially through the cone from the proximal cone end to the distal cone end. The channel is formed by an inner cone surface. The term "annular" comprises, in an axial plan view of the cone, bodies comprising a circular, elliptical, angular, e.g., quadrangular, pentagonal, or hexagonal, and irregular circumference, wherein bodies comprising an elliptical circumference are preferred due to better implantability in a patient, in particular in a bone canal of a patient.

The cone can be formed in one piece or by a plurality, i.e., by two or more annular cone segments, which are connected—in particular, reversibly connected—to one another. The cone can be formed, for example, from 2 to 20 cone segments, preferably from 4 to 15, more preferably from 4 to 10 cone segments.

Each cone segment forms an annular section of the cone and a corresponding disk-shaped section of the channel of the cone. The cone segments are "stacked on top of one another" such that they form the cone.

The cone segments comprise a cone segment outer diameter, wherein the respective outer cone segment diameters of the individual cone segments differ. The cone segment comprising the largest outer cone segment diameter forms the proximal cone end, wherein the cone segment outer diameter of the cone segments adjoining in the distal direction continues to decrease until, finally, the cone segment comprising the smallest outer cone segment diameter forms the distal cone end. The cone segments comprise cone segment outer diameters in a range of 20 to 60 mm, preferably 25 to 55 mm, more preferably 30 to 55 mm. In the case of cone segments comprising an elliptical circumference in an axial plan view, the cone segment outer diameter is understood to mean the length of the main axis, i.e., the longer of the axes extending through the center. This allows a good adaptation of the cone size to the anatomical specifications of a patient.

The cone segments can comprise different construction heights. For example, the individual cone segments have an overall height in the range of 1 mm to 10 mm, preferably in the range of 2 mm to 8 mm. This allows a fast, effective, and at the same time sufficiently small-scale adjustment of the axial extension of the augmentation device.

The channel serves to receive and fix a stem of a prosthesis, in particular a joint endoprosthesis or a revision joint endoprosthesis. For this purpose, the stem of the corresponding prosthesis can be inserted into the channel, in particular from a proximal channel end facing the proximal cone end. The channel comprises a channel diameter which is determined by a cone inner diameter. In one embodiment, the cone inner diameter is designed to be constant over the entire axial extension of the channel or the cone, which leads to a constant channel diameter over the entire course of the channel. In a further preferred embodiment, the cone inner diameter decreases—preferably uniformly—to the cone outer diameter from the proximal cone end in the direction of the distal cone end. In this embodiment, the cone comprises a cone wall thickness that is substantially equal over the entire axial extension of the cone, and, at the same time, the channel diameter decreases from the proximal cone end in the direction of the distal cone end.

The cone wall thickness can, for example, be in a range of 2 mm to 30 mm, preferably 2 mm to 15 mm, more preferably 2 mm to 10 mm.

The cone comprises a lateral surface. The lateral surface is arranged opposite the cone inner surface and at least partially represents a cone outer surface. In one embodiment, the lateral surface corresponds to the cone outer surface.

At least two, i.e., two or more than two, metal plates—in particular, bent metal plates—are arranged in a reversibly detachable manner on the lateral surface of the cone. The metal plates can be attached to one another in a disjoint manner and can each be repeatedly detached from the lateral surface and re-attached, for example, by application or pressing.

The metal plates are arranged on the cone such that the lateral surface is at least partially encased by the metal plates, and the metal plates thus form at least a part of an augmentation device outer surface facing the bone in the implanted state. Preferably, the metal plates are arranged on the lateral surface without overlap.

The metal plates are shaped such that they are arranged on the cone—in particular, on the lateral surface of the cone—following an outer contour of the cone. In one embodiment of the augmentation device, the metal plates are in form-fitting contact with the outer surface of the cone. The lateral surface of the cone is in this case convex, and a metal plate inner surface of the metal plates is designed to be concave, i.e., curved, following the contour of the lateral surface. Preferably, a metal plate outer surface of the metal plates arranged opposite the metal plate inner surface is convex. More preferably, the metal plates comprise a uniform metal plate wall thickness.

In order to implant the augmentation device into a bone—in particular, a bone canal—it is pushed with metal plates arranged on the lateral surface with the distal cone end in front of the prepared implant site of the bone. The metal plates are pressed against the bone tissue by a force acting on the cone from the direction of the proximal cone end, and the augmentation device is thus fixed in the implant site. The cone represents an abutment for the metal plates. After the augmentation device has been fixed in the implant site, a prosthesis—in particular, a stem of a prosthesis—can be inserted into the channel of the augmentation device from the direction of the proximal cone end and anchored there—for example, by means of bone cement.

Should it be necessary to explant the implant, the prosthesis to be removed—in particular, the revision joint endoprosthesis—can be pulled out of the augmentation device axially in the direction of the proximal cone end. Preferably, the cone is substantially not connected to bone tissue via growth or ingrowth, so that, depending upon the anchoring of the prosthesis to the cone, e.g., in the case of fixed anchoring by means of a bone cement, the cone is simultaneously removed from the bone when the prosthesis is pulled out. The cone can be detachably displaced axially in the direction of the proximal conical end against the metal plates in order to reversibly separate the metal plates and the cone. This represents a fast, simple, and safe explantation of the prosthesis.

The metal plates, which are preferably grown together with bone tissue, remain on the bone after the cone has been removed. Since the abutment, which presses the metal plates against the bone, was removed when the cone was removed, the metal plates can be pulled radially in the direction of the longitudinal axis of the bone and thus be detached from the bone. This results in less loss of bone tissue than an axial pulling motion performed along the length of the bone and facilitates explantation of the augmentation device. In addition, this reduces the risk of a high loss of bone tissue.

The metal plates serve to improve growth—in particular, ingrowth—of bone tissue onto or into the augmentation device in the implanted state.

Growth or ingrowth of bone tissue onto or into the cone is preferably prevented. This is achieved, for example, by the fact that, in the implanted state, the cone substantially does not come into contact with bone tissue, in particular since the cone is encased in a substantially collar-like manner by the metal plates. In a further embodiment, the cone is not formed from metal, so that a growth or ingrowth of bone tissue onto or into the cone is substantially eliminated.

In order to further facilitate explantation of the augmentation device and to further minimize the risk of a high loss of bone tissue during explantation, in one embodiment of the augmentation device, the metal plates are arranged on the lateral surface of the cone such that they are spaced apart from one another by gaps extending axially in the longitudinal direction of the augmentation device. The number of gaps depends upon the number of metal plates. For example, two metal plates are arranged on the lateral surface of the cone such that they are spaced apart from one another by two gaps.

In one embodiment, at least one of the gaps and the longitudinal axis of the device extend in a common plane. Preferably, the gaps of the augmentation device with arranged metal plates extend along the shortest path from the proximal cone end to the distal cone end.

The gaps between the metal plates are also retained in the implanted state of the augmentation device, so that the metal plates can be pulled more easily radially in the direction of the longitudinal axis of the bone, and thus removed from the bone during explantation after the cone has been detached from the metal plates by axially displacing the cone in the direction of the proximal cone end. By means of the axially extending gaps, each of the metal plates can be removed by a radial pulling motion in the direction of the longitudinal axis of the bone, without being sterically hindered by one or more further metal plates still connected to the bone tissue.

The gaps can be of different sizes in order to space the metal plates on the lateral surface of the cone. In order to ensure facilitated explantation, it is preferable for at least one of the gaps, preferably all gaps, to have a gap width in a range of 1 mm to 5 mm, preferably in a range of 2 mm to 5 mm, and more preferably in a range of 3 mm to 4 mm. A smaller gap width would contribute less to facilitated explantation of the augmentation device, whereas a larger gap width leads to smaller metal plates, so that growth or ingrowth of bone tissue onto or into the augmentation device is reduced.

One embodiment of the augmentation device is characterized in that the lateral surface of the cone, axially extending webs are formed which engage in the gaps—in particular, the axially extending gaps—between the metal plates, so that the webs fill the gaps at least partially, preferably substantially completely. Preferably, the webs extend over the entire axial extension of the cone. In one embodiment, the cone and the webs are designed in multiple parts, wherein the cone and the webs are connected to one another, e.g., by means of an adhesive connection or a force-fitting connection. In a further preferred embodiment, the cone and the webs are designed in one piece. The webs facilitate the arrangement of the metal plates on the lateral surface, so that each metal plate can be attached to the lateral surface at its intended position. In addition, the webs prevent displacement of the metal plates on the lateral surface and in particular prevent the metal plates from rubbing against one another, which could lead to undesired metal abrasion, in particular in the implanted state of the augmentation device. Furthermore, the webs prevent the gaps between the metal plates from growing with tissue—in particular, bone tissue and connective tissue—in the implanted state of the augmentation device, so that, when the augmentation device is explanted after the cone has been removed, the connected metal plates can be more easily detached from the bone tissue by radial traction in the direction of the longitudinal axis of the bone.

The webs can be solid or structured, for example, with a honeycomb structure.

One embodiment of the augmentation device is characterized in that the webs comprise at least one fluid-conducting web guide means which fluidically connects the proximal cone end to the distal cone end, the proximal cone end to a web outer surface, or the proximal cone end to the distal cone end, and the proximal cone end and the web outer surface. By means of the at least one web guide means, pharmaceutical fluids, such as aqueous antibiotic solutions, can be conveyed from the proximal cone end, which is easily accessible for the surgeon after implantation of the augmentation device in the corresponding implant site, in the direction of the distal cone end. In the case of a web guide means which fluidically connects the proximal cone end to the distal cone end, pharmaceutical fluids can be conveyed at least to the distal region of the augmentation device. In the case of a web guide means which fluidically connects the proximal cone end to a web outer surface, pharmaceutical fluids can be conveyed at least to the region of the lateral surface of the cone, and thus to the region of the circumference of the augmentation device. In one embodiment, the web guide means opens at a web outer surface facing away from the channel. In a further, preferred embodiment, the web guide means opens at least on a web outer surface facing the metal plates. In this case, the web guide means can open at one or more points on the web outer surface facing the metal plates. If the web guide means opens on a web outer surface facing the metal plate, the risk of tissue ingrowth—in particular, bone tissue or connective tissue—into the web guide means is reduced, since this is partially shielded by the metal plate and thus makes tissue ingrowth more difficult. If the web guide means leads to a web outer surface facing the metal plate, it is preferred that the metal plate comprise at least one groove in the metal plate outer surface and/or metal plate inner surface—in particular, a groove extending radially and/or axially over the entire extension of the metal plate—which groove is fluidically connected to the web guide means and ensures a more extensive distribution of the pharmaceutical fluid on the augmentation device outer surface. Preferably, each mouth of the web guide means is fluidically connected to a groove. In one embodiment, a web guide means fluidically connects both the distal cone end and a web outer surface of the web to the proximal cone end.

Preferably, all webs of the augmentation device comprise at least one web guide means.

A web guide means is understood to mean any type of structure which extends at least in sections within the web and which allows a fluid, such as a liquid or a gas, to be conveyed from one end of the web guide means to a further end of the web guide means. The web guide means can, for example, be a bore, a hose, or a tunnel.

One embodiment of the augmentation device is characterized in that the cone comprises at least one cone guide means which fluidically connects the proximal cone end and the distal cone end to one another. By means of the at least one cone guide means, pharmaceutical fluids, such as aqueous antibiotic solutions, can be conveyed from the proximal cone end, which is easily accessible for the surgeon after implantation of the augmentation device in the corresponding implant site, to the distal cone end.

A cone guide means is understood to mean any type of structure which extends at least in sections within the cone and which allows a fluid, such as a liquid or a gas, to be conveyed from a proximal end of the cone guide means to a distal end of the cone guide means. The cone guide means can, for example, be a bore, a hose, or a tunnel.

One embodiment of the augmentation device is characterized in that the cone comprises a sliding element at the proximal cone end, which sliding element interacts with the metal plates at a proximal metal plate end facing the proximal cone end such that a force acting on the cone from the direction of the proximal cone end can be transmitted to the metal plates via the sliding element. The sliding element extends at least partially radially beyond or out of the lateral surface of the cone and is arranged proximally to the proximal metal plate end. Preferably, the sliding element is formed as a radially circumferential bead at the proximal cone end. If a force is applied from the direction of the proximal cone end, this force acts on the sliding element in the direction of the distal cone end and is transmitted via its distal sliding element surface facing the metal plate to the proximal metal plate end facing the sliding element and thus displaces the metal plate together with the cone in the direction of the distal cone end. As a result, the sliding element ensures an improved force application on the metal plates and reduces the undesired slippage of the metal plates from the lateral surface during the insertion of the augmentation device into an implant site.

In one embodiment of the augmentation device, the metal plate inner surface and the lateral surface are designed to be smooth, so that the cone can be reversibly detached from the metal plates by the lowest possible force application on the cone in the direction of the proximal cone end.

One embodiment of the augmentation device is characterized in that the metal plates are arranged on the lateral surface of the cone such that a reversible, form-fitting connection is formed between the metal plates and the lateral surface. The reversible, form-fitting connection serves to prevent the metal plates from unintentionally detaching from the lateral surface of the cone—for example, during transport or implantation of the augmentation device. The form-fitting connection furthermore allows the cone and metal plates to be detached by axial pulling of the cone in the direction of the proximal cone end. In one embodiment, the form-fitting connection between the metal plates and the cone—in particular, the lateral surface of the cone—is designed as a tongue-and-groove connection. In a further embodiment, the form-fitting connection between the metal plates and the cone—in particular, the lateral surface of the cone—is designed as a knob-like or clamping component-like connection.

The metal plates and the cone can comprise wall thicknesses of different sizes.

One embodiment of the augmentation device is characterized in that a cone wall thickness of the cone is greater than or equal to a metal plate wall thickness of the metal plates. It is thus ensured that the cone can serve as an abutment for the metal plates that is as stable as possible during implantation and in the implanted state of the augmentation device. In addition, a press fit anchoring of the augmentation device in the implant site is thus facilitated. The cone wall thickness is preferably in a range of 2 mm to 30 mm, preferably in a range of 2 mm to 15 mm, more preferably in a range of 2 mm to 10 mm. The metal plate wall thickness is preferably in a range of 1.5 mm to 15 mm, preferably in a range of 1.5 mm to 10 mm, more preferably in a range of 1.5 mm to 5 mm.

The metal plates can cover different-sized surface areas of the lateral surface of the cone.

In order to allow good growth or ingrowth of bone tissue onto or into the augmentation device—in particular, the metal plates—and thus a stable anchoring of the augmentation device in an implant site, one embodiment of the augmentation device is characterized in that the metal plates cover at least 80% by area, preferably at least 90% by area, more preferably at least 95% by area of the lateral surface, based on the total area of the lateral surface.

One embodiment of the augmentation device is characterized in that the metal plate outer surface facing away from the lateral surface of the cone is roughened, porous—in particular, open pored—and/or comprises blind holes. The metal plate outer surface structured in this way facilitates growth or ingrowth of bone tissue and thus improves anchoring of the augmentation device in an implant site. Preferably, the blind holes extend substantially radially, in particular perpendicularly, to the longitudinal axis of the augmentation device. The blind holes are preferably not connected to one another, so that no undercuts are formed on the blind holes, which would impede an explantation of the metal plates from an implant site. The roughened structure of the outer surface of the metal plate can be achieved, for example, by sandblasting, in particular by coarse sandblasting.

In order to achieve improved ingrowth of bone tissue, one embodiment of the augmentation device is characterized in that the blind holes comprise a diameter of less than 3 mm, preferably of less than 2 mm, more preferably of less than 1 mm, wherein the diameter is preferably not less than 0.5 mm. This range enables good ingrowth of bone tissue into the metal plates and is easy to manufacture.

An intermediate space can be formed between the metal plates and the cone, in particular between the metal plate inner surfaces and the lateral surface of the cone. The intermediate space can, for example, be created intentionally, e.g., by indentations in the metal plates and/or the cone, be caused by production technology, and/or be due to the metal plates slipping on the lateral surface during implantation of the augmentation device in an implant site. In order to reduce or completely avoid material abrasion, one embodiment of the augmentation device is characterized in that the cone comprises at least one feedthrough which fluidically connects the channel to the intermediate space between the cone and at least one of the metal plates. This allows a bone cement paste, which is applied, for example, to anchor a prosthesis in the channel, to be conveyed through the at least one feedthrough into the intermediate space. The intermediate space can be filled via the at least one feedthrough with the bone cement paste, which hardens there to form a bone cement. The bone cement in the intermediate space between the cone and the at least one metal plate effectively prevents micromovements and reduces or prevents material abrasion as a result.

One embodiment of the augmentation device is characterized in that a scraper element is arranged on a distal channel end facing the distal cone end. The scraper element serves to ensure that bone cement paste, which is filled into the channel—in particular, into the proximal channel end—remains largely in the channel and is not discharged from the distal channel end. At the same time, the scraper element allows a prosthesis stem to be guided through the channel for anchoring a prosthesis in the augmentation device. For this purpose, the prosthesis stem can be pushed through the channel and through the scraper element from the direction of the proximal channel end, so that the prosthesis stem protrudes at least in sections from the distal channel end. When the prosthesis stem is pushed through the scraper element, the scraper element largely scrapes off bone cement paste adhering to the prosthesis stem, so that the bone cement remains within the channel, and a prosthesis stem largely free of bone cement paste emerges from the distal channel end. The scraper element can be shaped in different ways in order to achieve the desired effect. For example, the scraper element can be designed as a plate—in particular, an elastically deformable plate, e.g., made of a polymer—which comprises a recess substantially in the form of a cross-sectional geometry of a prosthesis stem. The plate fluidically closes the distal channel end for bone cement paste, with the exception of the recess through which the prosthesis stem can be pushed axially. As it is pushed through the recess, the scraper element, which is substantially in contact with the prosthesis stem, scrapes off the bone cement paste adhering to the prosthesis stem.

In a further embodiment, the scraper element is also designed as a plate—in particular, an elastically deformable plate, e.g., made of a polymer—wherein the plate comprises, instead of the recess, at least two, e.g., two, three, or four, notches which intersect at a point. The notches form plate sections which, in the rest state, substantially fluidically close the distal channel end for bone cement paste. With high pressure application—in particular, by a prosthesis stem pushed through the channel from the proximal channel end—the plate sections bend out of the distal channel end, whereby a prosthesis stem can be pushed out of the distal channel end. In this case, the plate sections scrape off bone cement paste adhering to the prosthesis stem, so that the prosthesis stem is substantially free of bone cement paste.

One embodiment of the augmentation device is characterized in that the metal plates comprise a biocompatible metal, and preferably in that the metal plates consist of a biocompatible metal. Examples of biocompatible metals are titanium, titanium alloys, tantalum, tantalum alloys, and stainless steels, wherein titanium and titanium alloys are preferred.

The cone can comprise different materials or consist of different materials.

In order to prevent or at least impede the growth or ingrowth of bone tissue onto or into the cone as much as possible, one embodiment of the augmentation device is characterized in that the cone comprises a biocompatible polymer, and preferably in that the cone consists of a biocompatible polymer. Examples of biocompatible polymers are polyetherketone, polyamide, polyimide, polysulfone, and bone cement—in particular, PMMA bone cement—wherein bone cement—in particular, PMMA bone cement—is preferred. A cone made of bone cement—in particular, PMMA bone cement—improves the fixation of a prosthesis within the augmentation device by means of a bone cement, in particular PMMA bone cement.

The biocompatible polymer—in particular, the PMMA bone cement—can contain one or more pharmaceutical active ingredients, in particular one or more antibiotics. Preferred antibiotics in this case are gentamicin and tobramycin. The pharmaceutical active ingredients contained in the cone—in particular, antibiotics—can be released, at least via the proximal cone end and the distal cone end, after the augmentation has been implanted in an implant site.

Bone cement paste is understood to mean a substance that is suitable, in the field of medical technology, for creating a stable connection between artificial joints, such as hip and knee joints, and bone tissue, and/or for stabilizing vertebral bodies. By curing, a bone cement paste becomes a bone cement. These bone cements are preferably polymethyl methacrylate bone cements (PMMA bone cements) or inorganic bone cements.

PMMA bone cements have been used for a long time in medical applications and are based upon the work of Sir Charnley (cf. Charnley, J., Anchorage of the femoral head prosthesis of the shaft of the femur. *J. Bone Joint Surg.* 1960; 42, 28-30.). In this case, PMMA bone cements can be produced from a powder component comprising a bone cement powder as the first starting component and a liquid component comprising a monomer liquid as the second starting component. With a suitable composition, the two starting components can be storage-stable, separately from one another. When the two starting components are brought into contact with one another, a plastically-deformable bone cement paste is produced by the swelling of the polymer components of the bone cement powder. In this case, polymerization of the monomer by radicals is initiated. As the polymerization of the monomer progresses, the viscosity of the bone cement paste increases until it cures completely.

Bone cement powder is understood to mean a powder that comprises at least one particulate polymethyl methacrylate and/or a particulate polymethyl methacrylate copolymer. Examples of copolymers are styrene and/or methyl acrylate. In one embodiment, the bone cement powder can additionally comprise a hydrophilic additive which supports the distribution of the monomer liquid within the bone cement powder. In a further embodiment, the bone cement powder can additionally comprise an initiator which initiates the polymerization. In a further embodiment, the bone cement powder can additionally comprise a radiopaque material. In yet another embodiment, the bone cement powder can additionally comprise pharmaceutically-active substances, such as antibiotics.

The bone cement powder preferably comprises, as a hydrophilic additive, at least one particulate polymethyl methacrylate and/or a particulate polymethyl methacrylate copolymer, an initiator, and a radiopaque material, or consists of these components. More preferably, the bone cement powder comprises at least one particulate polymethyl methacrylate and/or a particulate polymethyl methacrylate copolymer, an initiator, a radiopaque material, and a hydrophilic additive, or consists of these components. Most preferably, the bone cement powder comprises at least one particulate polymethyl methacrylate and/or a particulate polymethyl methacrylate copolymer, an initiator, a radiopaque material, a hydrophilic additive, and an antibiotic, or consists of these components.

According to the invention, the particle size of the particulate polymethyl methacrylate and/or the particulate polymethyl methacrylate copolymer of the bone cement powder of the sieve fraction can correspond to less than 150 μm, preferably less than 100 μm.

According to the invention, the hydrophilic additive can be designed in particulate and/or fibrous form. In a further embodiment, the hydrophilic additive can be slightly soluble, and preferably insoluble, in methyl methacrylate. In a further embodiment, the hydrophilic additive can have an absorption capacity of at least 0.6 g methyl methacrylate per gram of hydrophilic additive. In a further embodiment, the hydrophilic additive can comprise a chemical substance comprising at least one OH group. In this case, the hydrophilic additive can preferably have covalently-bonded OH groups at its surface. Examples of such preferred hydrophilic additives can be additives selected from the group comprising cellulose, oxycellulose, starch, titanium dioxide, and silicon dioxide, wherein pyrogenic silicon dioxide is particularly preferred. In one embodiment, the particle size of the hydrophilic additive can correspond to the sieve fraction of less than 100 μm, preferably less than 50 μm, and most preferably less than 10 μm. The hydrophilic additive can be contained in an amount of 0.1 to 2.5% by weight, based on the total weight of the bone cement powder.

According to the invention, the initiator can contain dibenzoyl peroxide or consist of dibenzoyl peroxide.

According to the invention, a radiopaque material is understood to mean a substance that makes it possible to make the bone cement visible on diagnostic X-ray images. Examples of radiopaque materials can include barium sulfate, zirconium dioxide, and calcium carbonate.

According to the invention, the pharmaceutically-active substance can comprise one or more antibiotics and, optionally, added cofactors for the one or more antibiotics. Preferably, the pharmaceutically-active substance consists of one or more antibiotics and, optionally, added cofactors for the one or more antibiotics. Examples of antibiotics include, inter alia, gentamicin, clindamycin, and vancomycin.

According to the invention, the monomer liquid can comprise the monomer methyl methacrylate or consist of methyl methacrylate. In one embodiment, the monomer liquid comprises, in addition to the monomer, an activator dissolved therein, such as N,N-dimethyl-p-toluidine, or consists of methyl methacrylate and N,N-dimethyl-p-toluidine.

An inorganic bone cement is understood to mean a bone cement based upon calcium phosphates and calcium sulfate dihydrate. Powders of calcium phosphates and/or calcium sulfate dihydrate that can be cured by a liquid component comprising an aqueous solution of different salts are used as powder components in this case. A large number of inorganic bone cements have been described, of which the following are mentioned by way of example: EP 1 592 463 B1, EP 2 271 585 B1, and EP 2 988 789 B1.

FIGURES

In the following, the invention is illustrated further, by way of example, by figures. The invention is not limited to the figures.
Shown are:

FIG. 1 a schematic perspective side view of an augmentation device in a separate state, FIG. 2 the augmentation device from FIG. 1 in a perspective side view in an assembled state, FIG. 3 a schematic perspective side view of a further augmentation device, FIG. 4 a schematic exploded view of a further augmentation device, FIG. 5 a schematic perspective sectional view of a further augmentation device, FIG. 6 a schematic perspective sectional view of a further augmentation device, FIG. 7 a schematic perspective side view of a further augmentation device in a separate state, FIG. 8 a schematic perspective side view of a further augmentation device.

Figure 1:
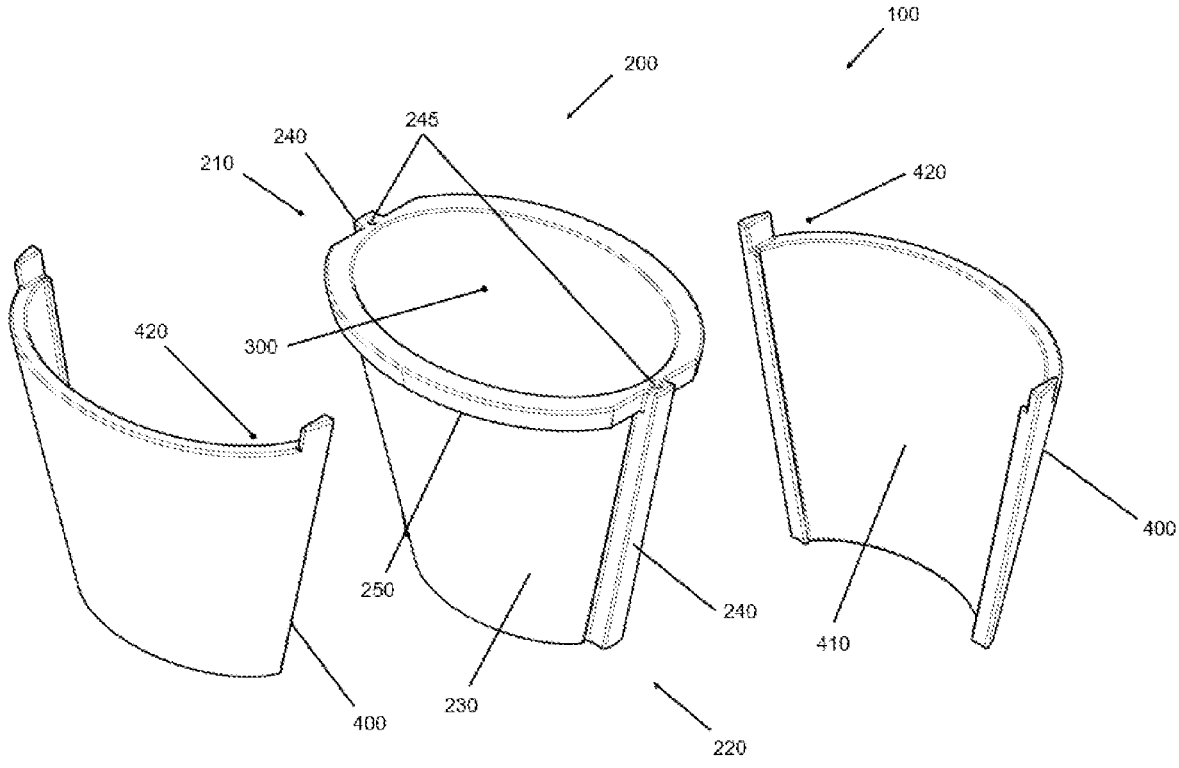
FIG. 1 is a schematic side view of an augmentation device 100 in a separate state. The augmentation device 100 comprises an annular cone 200 through which a fluid-conducting channel 300 extends axially from a proximal cone end 210 to a distal cone end 220. The cone 200 comprises an outer diameter which decreases from the proximal cone end 210 in the direction of the distal cone end 220. The cone 200 comprises an elliptical cross-section.

The cone 200 comprises a lateral surface 230 and two, axially extending webs 240 facing one another on the lateral surface 230 (only one of the webs 240 is completely visible). The cone 200 and the webs 240 are formed in one piece. A channel-like web guide means 245, which fluidically connects the proximal cone end 210 to the distal cone end 220, extends axially through each of the webs 240. The web guide means 245 allow a pharmaceutical fluid, e.g., an aqueous antibiotic solution, to be applied, via the proximal cone end 210, which is easily accessible for the surgeon in the implanted state of the augmentation device 100, to the distal cone end 220, which is difficult to access for the surgeon in the implanted state of the augmentation device 100.

In addition to the cone 200, the augmentation device 100 comprises two bent metal plates 400, wherein the metal plates are shaped such that they can be arranged, following an outer contour of the cone, in contact with the lateral surface 230. In FIG. 1, the cone 200 and the metal plates 400 of the augmentation device 100 are shown separately from one another.

The metal plates 400 are shaped in particular on a metal plate inner surface 410 facing the cone 200 such that the metal plates 400—in particular, the metal plate inner surface 410—follow the outer contour of the cone 200 such that the metal plates 400 can be arranged in contact with the lateral surface 230.

At the proximal cone end 210, the cone 200 further comprises a sliding element 250 extending radially around the cone 200, in particular the proximal cone end 210. The metal plates 400 each comprise a metal plate recess 420, into which the sliding element 250 can engage when the metal plates 400 are arranged on the lateral surface. This facilitates the arrangement and improves the adhesion of the metal plates 400 to the lateral surface 230.

Figure 2:
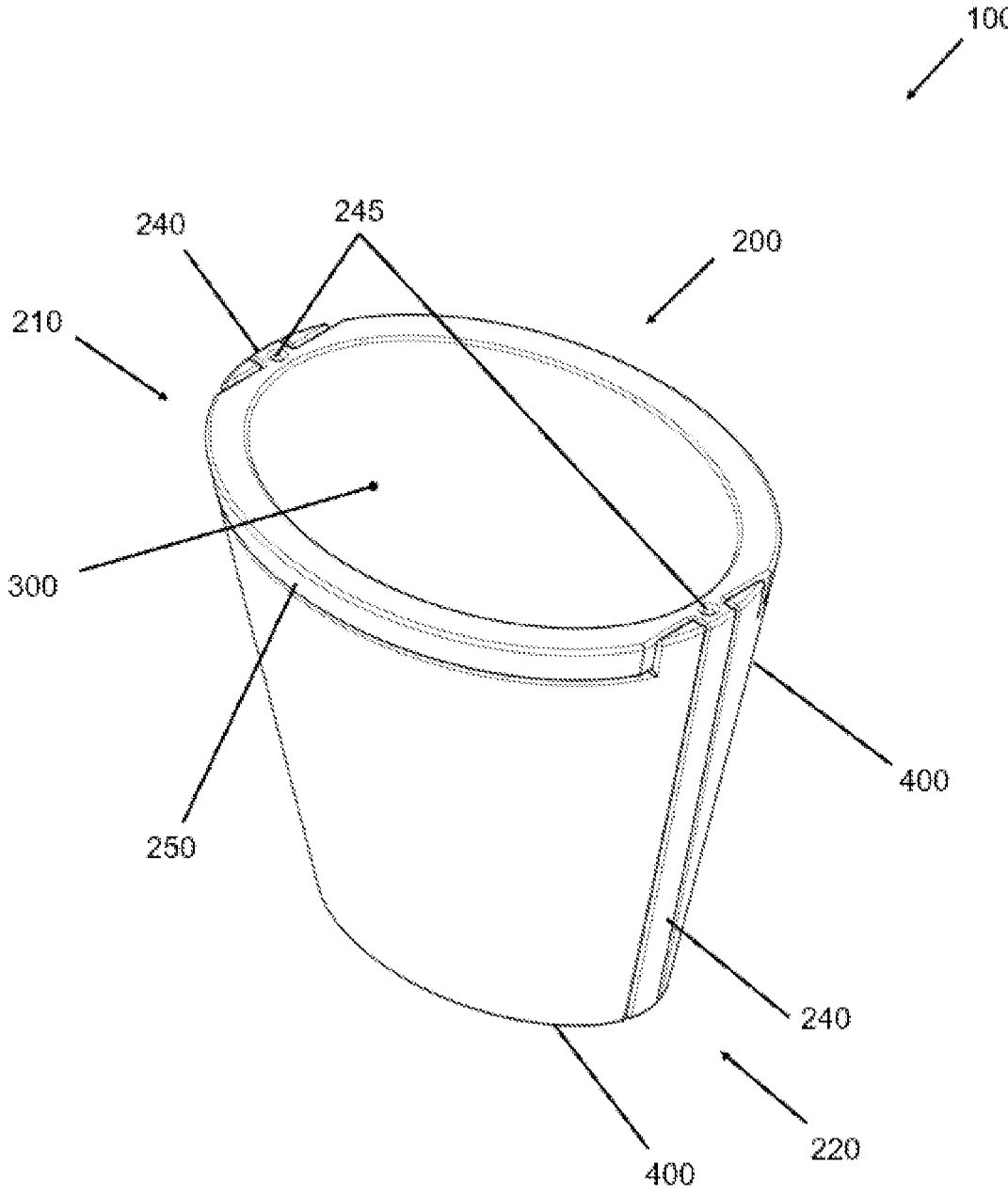

FIG. 2 shows the augmentation device 100 from FIG. 1 in a perspective side view in an assembled state. The metal plates 400 are arranged on the cone 200 and are in contact with the lateral surface 230 (cf. FIG. 1), so that the metal plate inner surfaces 410 (cf. FIG. 1) are substantially completely in contact with the lateral surface 230 (cf FIG. 1). In the assembled state, the sliding element 250 engages in the metal plate recesses 420 (cf FIG. 1), so that an axial force application on the cone 200 from the proximal cone end 210 in the direction of the distal cone end 220 is transmitted to the metal plates 400 via the sliding element 250. This facilitates the implantation of the augmentation device 100 in a patient and ensures that the metal plates 400 do not slip on the lateral surface 230 (cf FIG. 1) in the direction of the proximal cone end 210 during implantation. In the assembled state, the metal plates 400 are located both on the lateral surface 230 (cf FIG. 1) and on the webs 240. The metal plates 400 are spaced apart from one another by the webs 240. Between the metal plates 400, gaps (not shown) are formed, which are substantially completely filled by the webs 240. The webs 240 prevent unintentional slippage of the metal plates 400 on the cone 200.

Figure 3:
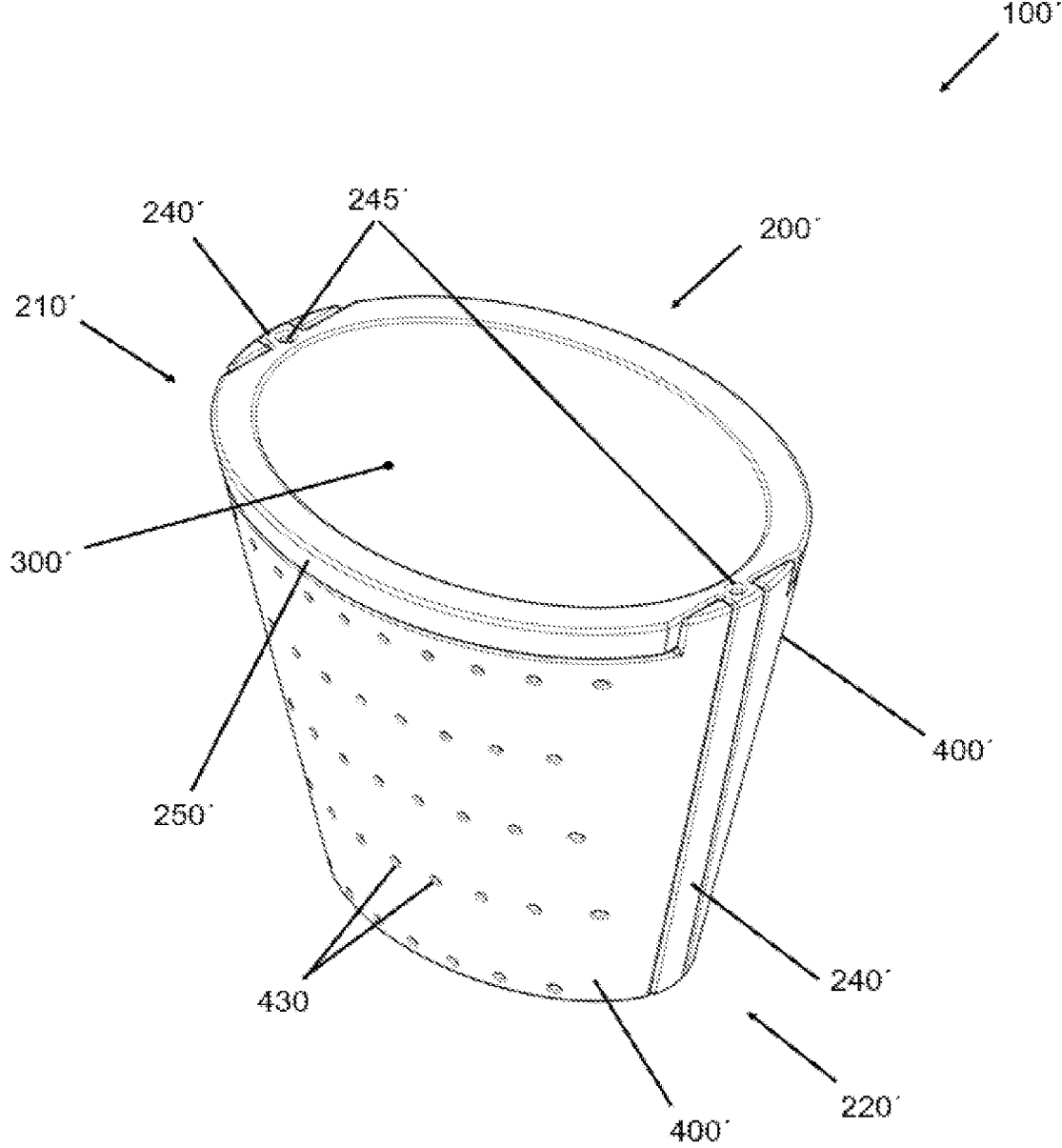

FIG. 3 is a perspective side view of a further embodiment of an augmentation device 100' in an assembled state. The embodiment of the augmentation device 100' largely corresponds to the embodiment described above and shown in FIGS. 1 and 2, and therefore reference is made to the above description in order to avoid repetition. Modifications to an embodiment shown in FIGS. 1 and 2 have the same reference sign with an additional apostrophe. The augmentation device 100' differs from the augmentation device 100 from FIGS. 1 and 2 by blind holes 430 present in the metal plates 400' (numbered only by way of example and only visible on the metal plate 400' facing the observer of the drawing). The blind holes 430 improve growth and ingrowth of bone tissue on and into the metal plates 400'.

Figure 4:
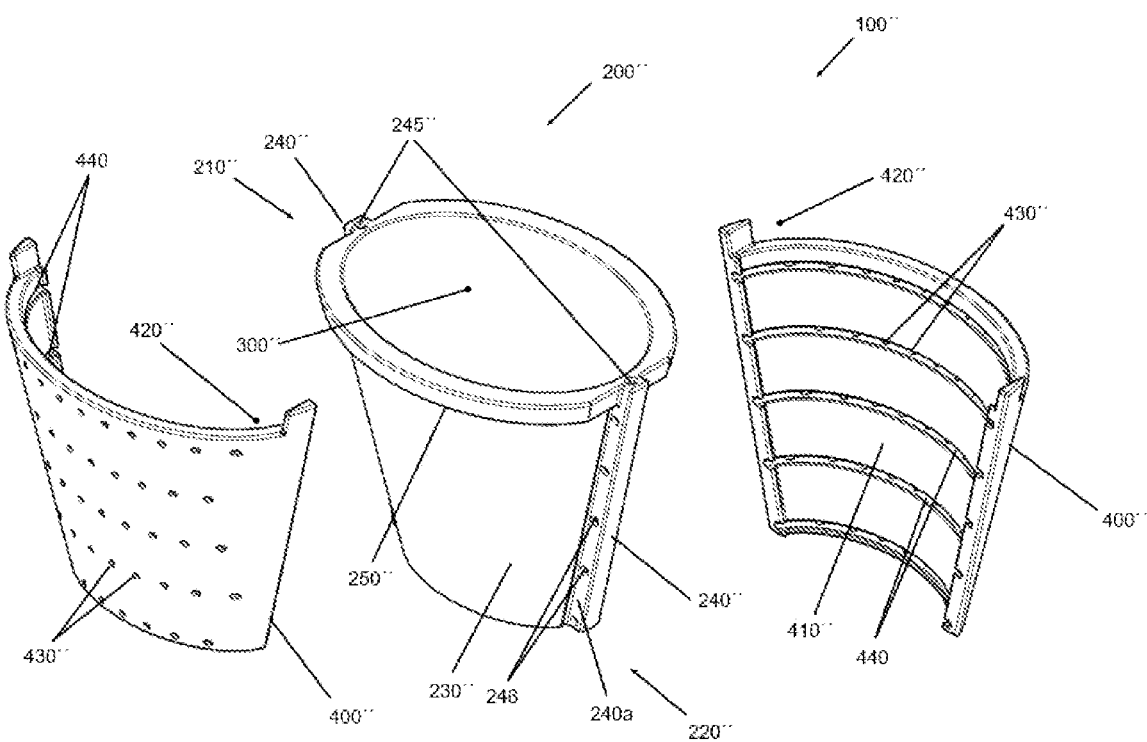

FIG. 4 is a perspective side view of a further embodiment of an augmentation device 100" in a separate state. The embodiment of the augmentation device 100" largely corresponds to the embodiments described above and shown in FIGS. 1 through 3, and therefore reference is made to the above description to avoid repetition. Modifications of any of the embodiments shown in FIGS. 1 through 3 have the same reference sign with two apostrophes. The embodiment of the augmentation device 100" differs from the embodiment of the augmentation device 100' from FIG. 3 in that the channel-like web guide means 245" extending axially through the webs 240" comprise further web guide means openings 246 (numbered only by way of example) on the outer web surfaces 240a facing the metal plates 400" in the assembled state of the augmentation device 10". As a result, a pharmaceutical fluid, e.g., an aqueous antibiotic solution, can be applied not only to the distal cone end 220", but, additionally, also over the axial extension of the augmentation device 100". In order to achieve as uniform a distribution as possible over the entire circumference of the augmentation device 100" when a pharmaceutical fluid is applied to the web guide means 245" at the proximal cone end 210", the further web guide means openings 246 are connected in a fluid-conducting manner to inner grooves 440 extending on the inner metal plate surfaces 410" in the assembled state of the augmentation device 100". The inner grooves 440 are in turn fluidically connected to the blind holes 430" in order to allow as uniform a distribution of a pharmaceutical fluid as possible over the circumference of the augmentation device 100".

Figure 5:
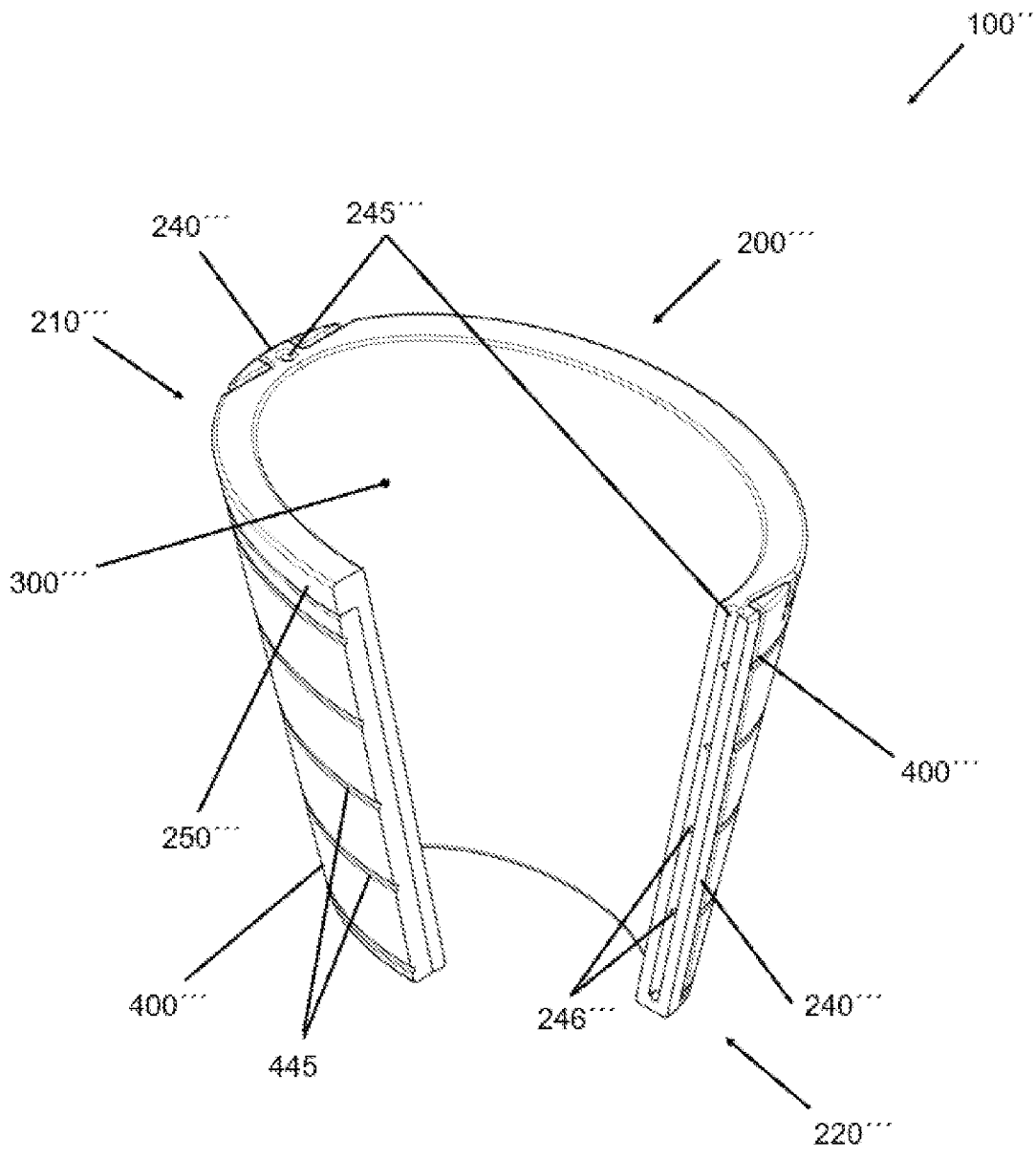

FIG. 5 is a sectional view of a perspective side view of a further embodiment of an augmentation device 100''' in an assembled state. The embodiment of the augmentation device 100''' largely corresponds to the embodiments described above and shown in FIGS. 1 through 4, and therefore reference is made to the above description to avoid repetition. Modifications of any of the embodiments shown in FIGS. 1 through 4 have the same reference sign with three apostrophes. The embodiment of the augmentation device 100''' differs from the embodiment of the augmentation device 100" according to FIG. 4 in that the metal plates 400''' do not comprise blind holes, and in that the web guide means openings 246''' of the web guide means 245''' facing the metal plates 400''' are not fluidically connected to inner grooves extending on the metal plate inner surfaces, but are fluidically connected to outer grooves 445 extending on the metal plate outer surface. The outer grooves 445 allow the most extensive possible distribution of a pharmaceutical fluid applied into the web guide means 245''' at the proximal cone end 210''' over the circumference of the augmentation device 100'''.

Figure 6:
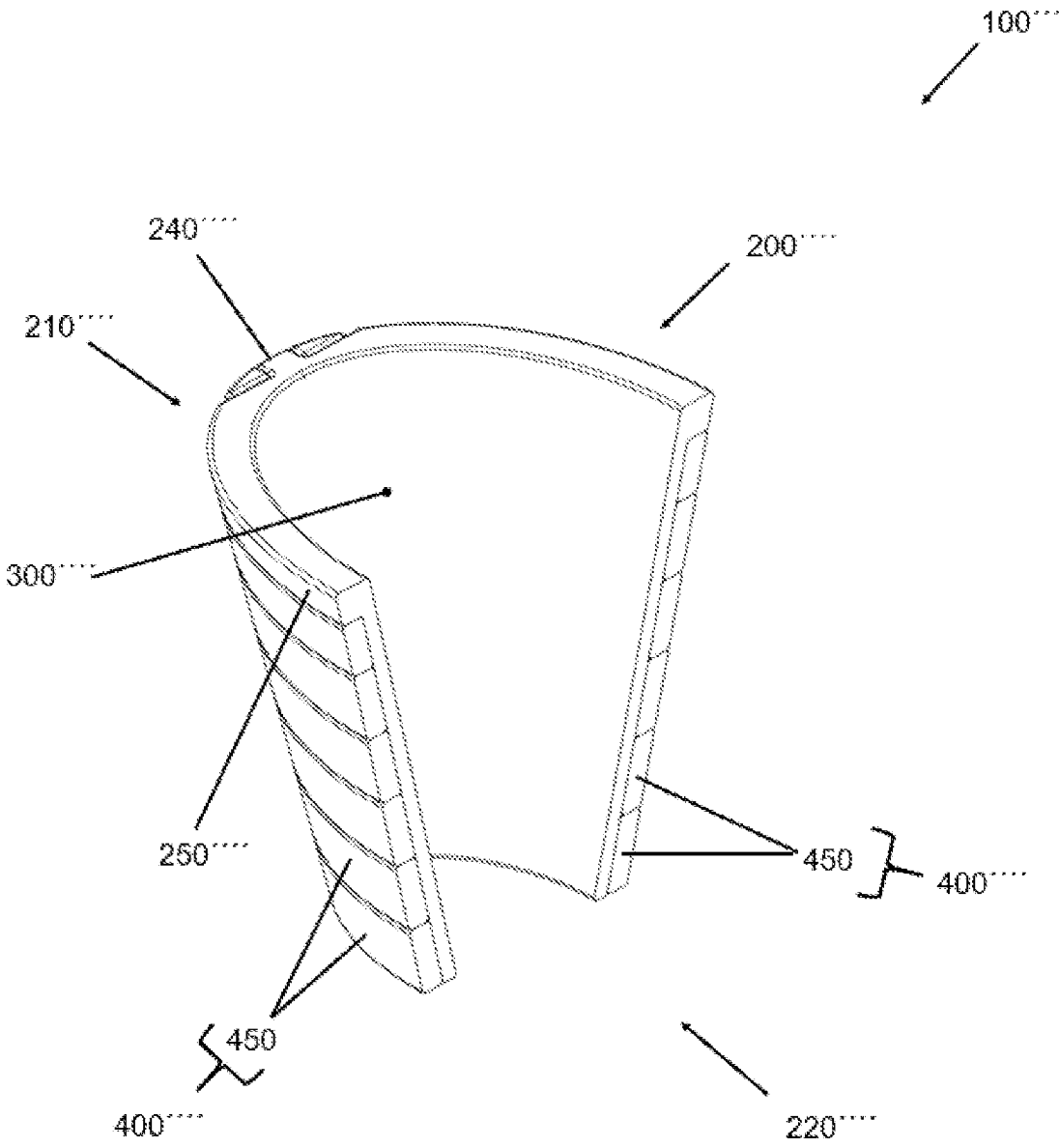

FIG. 6 is a sectional view of a perspective side view of a further embodiment of an augmentation device 100'''' in an assembled state. The embodiment of the augmentation device 100'''' largely corresponds to the embodiments described above and shown in FIGS. 1 through 5, and therefore reference is made to the above description to avoid repetition. Modifications of any of the embodiments shown in FIGS. 1 through 5 have the same reference sign with four apostrophes. The embodiment of the augmentation device 100'''' differs from the previous embodiments in that the metal plates 400'''' are formed on both sides of the cone 200'''' from a plurality of—in particular, from in each case six—metal plate segments 450 (numbered only by way of example). The individual metal plate segments 450 are reversibly separable from one another, as a result of which the metal plates 400'''' are quickly and easily adaptable in their axial extension along the longitudinal axis of the augmentation device 100''''. For example, the two metal plate segments 450 can be removed at the distal cone end 220'''', whereby the metal plates 400'''' are "shortened" around these two metal plate segments. Thus, anatomical specifics of a patient during an operation can be addressed quickly and easily.

Figure 7:
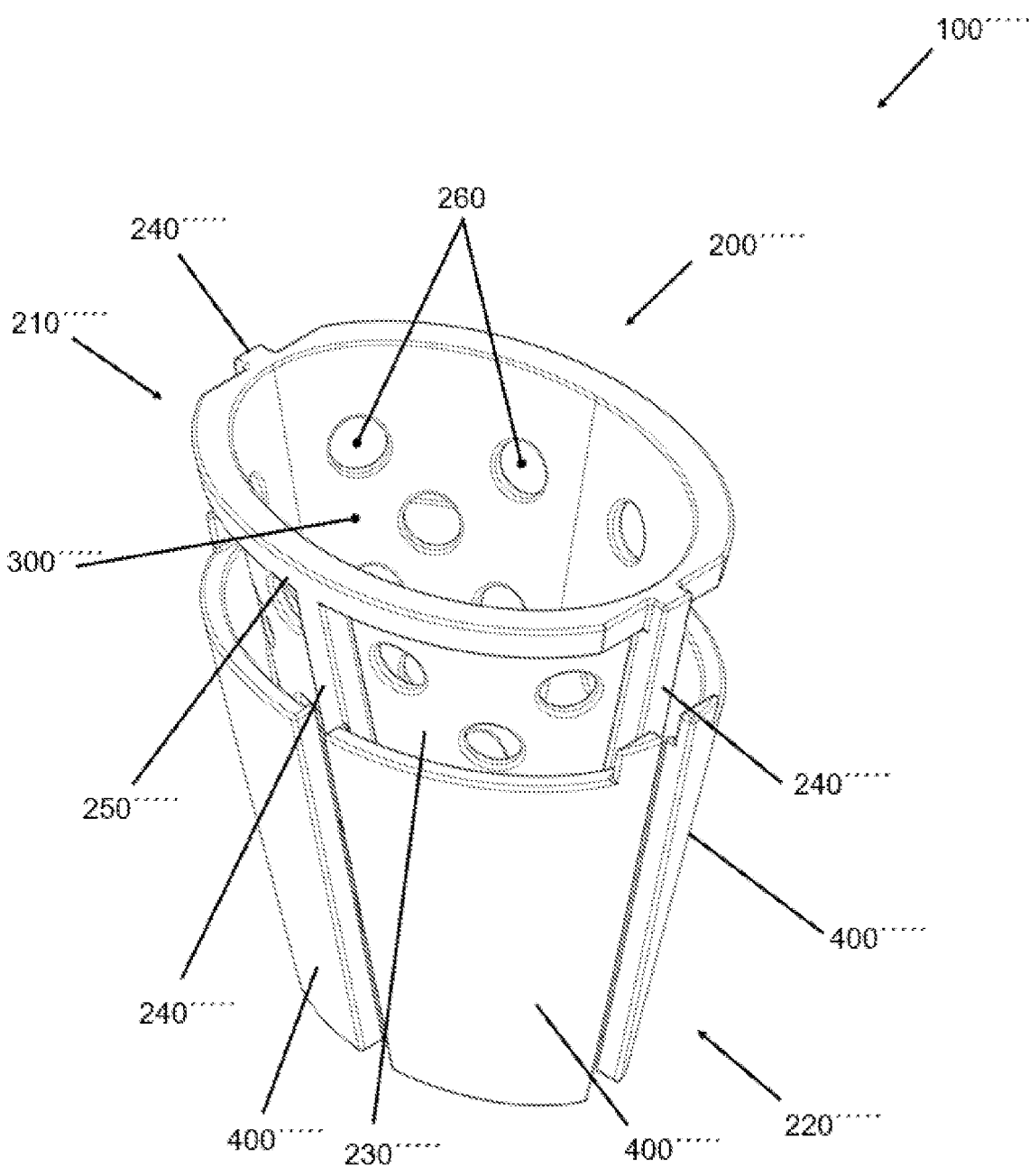

FIG. 7 is a perspective side view of a further embodiment of an augmentation device 100''''' in a separate state. The embodiment of the augmentation device 100''''' largely corresponds to the embodiments described above and shown in FIGS. 1 through 6, and therefore reference is made to the above description to avoid repetition. Modifications of any of the embodiments shown in FIGS. 1 through 6 have the same reference sign with five apostrophes. The embodiment of the augmentation device 100''''' differs from the previous embodiments in that the cones 200''''' comprise four, axially extending webs 240''''' distributed substantially uniformly over the lateral surface 230''''', and four metal plates 400'''''. The cone 20''''' comprises feedthroughs 260 (numbered only by way of example) which, in the assembled state of the augmentation device 100''''', fluidically connect the channel 300''''' and the metal plates 400''''' to one another. A bone cement paste, which is applied in the implanted state of the augmentation device 100′′′′′ into the channel via the proximal cone end 210′′′′′, can reach the metal plates 400′′′′′ through the feedthroughs 260 and fill any intermediate spaces between the metal plates 400′′′′′ and the lateral surface 230′′′′′ of the cone 200′′′′′. This reduces micromovements of the metal plates 400′′′′′ and reduces or prevents material abrasion, in particular metal abrasion.

Figure 8:
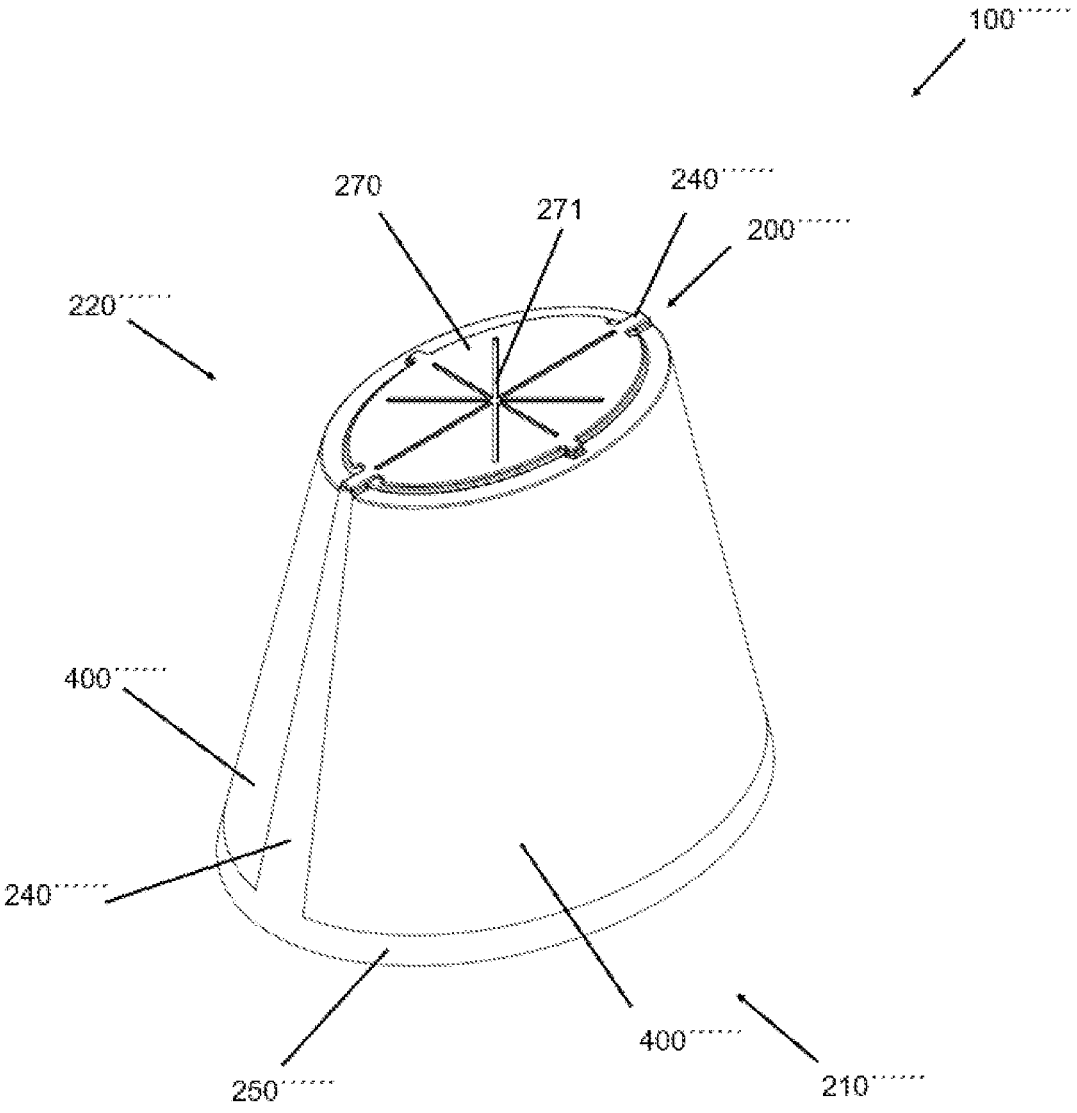

FIG. 8 is a perspective side view of a further embodiment of an augmentation device 100′′′′′ in an assembled state. The embodiment of the augmentation device 100′′′′′ largely corresponds to the embodiments described above and shown in FIGS. 1 through 7, and therefore reference is made to the above description to avoid repetition. Modifications of any of the embodiments shown in FIGS. 1 through 7 have the same reference sign with six apostrophes. At the distal cone end 220′′′′′, the augmentation device 100′′′′′ comprises a scraper element 270 which is fixedly connected to the cone 200′′′′′ and is designed as an elastically deformable plate comprising four notches 271 intersecting at one point (numbered only as an example). The notches 271 form plate sections in the plate of the scraper element 270. The scraper element 270 fluidically closes the distal cone end 220′′′′′ for bone cement paste (not shown) applied through the proximal cone end 210′′′′′ into the channel (not shown in FIG. 8; cf, for example, FIG. 1), so that the bone cement paste does not emerge from the distal cone end 220′′′′′ and remains within the channel. In conjunction with the notches 271, the elastic material of the scraper element 270 allows a stem of a prosthesis (not shown) to be pushed out through the channel from the direction of the proximal cone end 210′′′′′ by the bone cement paste located there and, by the scraper element 270, from the distal cone end 220′′′′′. In this case, the plate sections formed by the notches 271 in the scraper element 270 are bent outwards through the stem and scrape adhering bone cement off the stem as it is pushed out of the distal cone end 220′′′′′. The stem is thus, when it leaves the augmentation device 100′′′′′, substantially free of bone cement paste at the distal cone end 220′′′′′.

REFERENCE SIGNS

100, 100′, 100′′, 100′′′, Augmentation device
100′′′′, 100′′′′′, 100′′′′′′
200, 200′, 200′′, 200′′′, Cone
200′′′′, 200′′′′′, 200′′′′′′
210, 210′, 210′′, 210′′′, Proximal cone end
210′′′′, 210′′′′′, 210′′′′′′
220, 220′, 220′′, 220′′′, Distal cone end
220′′′′, 220′′′′′, 220′′′′′′
230, 230′′, 230′′′′ Lateral surface
240, 240′, 240′′, 240′′′, Web
240′′′′, 240′′′′′, 240′′′′′′
240a Web outer surface
245, 245′, 245′′, 245′′′ Web guide means
246 Web guide means opening
250, 250′, 250′′, 250′′′, Sliding element
250′′′′, 250′′′′′, 250′′′′′′
260 Feedthrough
270 Scraper element
271 Notch
300, 300′, 300′′, 300′′′ Channel
300′′′′, 300′′′′′, 300′′′′′′
400, 400′, 400′′, 400′′′, Metal plate
400′′′′, 400′′′′′, 400′′′′′′
410, 410′′ Metal plate inner surface
420, 420′′ Metal plate recess

430, 430′′ Blind hole
440 Inner groove
445 Outer groove
450 Metal plate segment

The invention claimed is:

1. An implantable augmentation device comprising an annular cone surrounding a channel which extends axially along a longitudinal axis of the augmentation device from a proximal cone end to a distal cone end,
    wherein an outer diameter of the cone decreases from the proximal cone end in the direction of the distal cone end,
    wherein the cone comprises a sliding element extending radially around the proximal cone end, a lateral surface, and two axially extending webs on the lateral surface diametrically opposed to each other,
    wherein at least two arched metal plates following an outer contour of the cone are arranged on the lateral surface of the cone,
    wherein the metal plates are spaced apart from one another by axially extending gaps between the metal plates,
    wherein the cone is reversibly detachable from the metal plates by displacing the cone in the direction of the proximal cone end,
    wherein the sliding element interacts with the metal plates at a proximal metal plate end facing the proximal cone end such that a force acting on the cone from the direction of the proximal cone end can be transmitted to the metal plates via the sliding element.
2. The augmentation device according to claim 1, wherein the metal plates are arranged on the lateral surface of the cone such that a reversible, form-fitting connection is formed between the metal plates and the lateral surface.
3. The augmentation device according to claim 1, wherein a cone wall thickness of the cone is greater than or equal to a metal plate wall thickness of the metal plates.
4. The augmentation device according to claim 1, wherein the metal plates cover at least 80% by area of the lateral surface of the cone.
5. The augmentation device according to claim 1, wherein a metal plate outer surface facing away from the lateral surface of the cone is roughened, porous, and/or comprises blind holes.
6. The augmentation device according to claim 5, wherein the blind holes comprise a diameter of less than 3 mm.
7. The augmentation device according to claim 1, wherein the cone comprises feedthroughs which fluidically connect the channel to an intermediate space between the cone and the metal plates.
8. The augmentation device according to claim 1, wherein a scraper element is arranged on a distal channel end facing the distal cone end.
9. The augmentation device according to claim 1, wherein the metal plates comprise a biocompatible metal.
10. The augmentation device according to claim 1, wherein the cone comprises a biocompatible polymer.
11. The augmentation device according to claim 1, wherein the cone further comprises channel-like web guide means, which channel-like web guide means extends axially through each of the axially extending webs and fluidically connecting the proximal cone end to the distal cone end, wherein the web guide means are sized and configured to allow a pharmaceutical fluid to be applied via the proximal cone end.

* * * * *